United States Patent [19]
Griffiths et al.

[11] Patent Number: 6,120,768
[45] Date of Patent: *Sep. 19, 2000

[54] DOTA-BIOTIN DERIVATIVES

[75] Inventors: Gary L. Griffiths, Morristown; Hans Hansen, Mystic Island; Serengulam V. Govindan, Summit, all of N.J.

[73] Assignee: Immunomedics, Inc., Morris Plains, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/990,843

[22] Filed: Dec. 15, 1997

Related U.S. Application Data

[63] Continuation-in-part of application No. 08/486,166, Jun. 7, 1995, abandoned, and application No. 08/688,781, Jul. 31, 1996, which is a continuation-in-part of application No. 08/409,960, Mar. 23, 1995, Pat. No. 5,736,119, which is a continuation of application No. 08/062,662, May 11, 1993, abandoned.

[51] Int. Cl.⁷ ................................................. A61K 39/395
[52] U.S. Cl. .................................. 424/178.1; 424/183.1; 424/1.53; 424/181.1; 424/9.1; 424/9.3; 424/1.49; 424/1.41; 530/324; 530/325; 530/326; 530/327; 530/328; 530/329; 530/330; 530/331
[58] Field of Search ............................... 424/178.1, 1.41, 424/1.49, 9.3, 9.1, 181.1, 183.1, 1.53; 530/324–331

[56] References Cited

U.S. PATENT DOCUMENTS

| | | | |
|---|---|---|---|
| 4,624,846 | 11/1986 | Goldenbeg et al. | 424/1.1 |
| 4,732,864 | 3/1988 | Tolman | 436/547 |
| 4,782,840 | 11/1988 | Martin, Jr. et al. | 128/654 |
| 4,863,713 | 9/1989 | Goodwin et al. | 424/1.1 |
| 4,932,412 | 6/1990 | Goldenberg | 128/654 |
| 5,202,451 | 4/1993 | Fritzberg et al. | |
| 5,283,342 | 2/1994 | Gustaavson et al. | |
| 5,326,778 | 7/1994 | Rosebrough | |
| 5,428,156 | 6/1995 | Mease et al. | 540/474 |
| 5,443,813 | 8/1995 | Hainfield | 530/391.3 |
| 5,525,338 | 6/1996 | Goldenberg et al. | 424/178.1 |
| 5,556,982 | 9/1996 | Fritzberg et al. | 548/303.7 |

FOREIGN PATENT DOCUMENTS

| | | |
|---|---|---|
| 496 074 | 7/1992 | European Pat. Off. |
| WO 91/14458 | 10/1991 | WIPO |
| WO 93/25240 | 6/1993 | WIPO |
| WO 95/15335 | 6/1995 | WIPO |

OTHER PUBLICATIONS

Kalofonos, H. P. et al., "Imaging of Tumor in Patients with Indium–111–Labeled Biotin and Streptavidin–Conjugated Antibodies: Preliminary Communication", Journal of Nuclear Medicine, 31:1791–1796 (1990).

Paganelli, P. et al., "Tumor Targeting in Patients with Ovarian Cancer Using Biotinylated Monoclonal Antibodies and Radioactive Streptavidin", Scientific Papers, Proceedings of the 37th Annual Meeting, vol. 31, No. 5 (May 1990).

Hainfeld, J. F., "Uranium–loaded Apoferritin with Antibodies Attached: Molecular Design for Uranium Neutron–capture Therapy", Proc. Natl. Acad. Sci. USA, vol. 89, 11064–11068 (Nov. 1992).

Osband, et al, Immuunol. Today, 11:193, 1990, Problems . . . immunotherapy.

Harris, et al. Tibtech, 11:42, 1993, Therapeutic . . . Age.

Goodwin "Tumor Pretargeting: Almost the Bottom Line," J. Nucl. Med. 36(5): 876–879 (May, 1995).

Hawkins et al. "Delivery of Radionuclides to Pretargeted Monoclonal Antibodies Using Dihydrofolate Reductase and Methotrexate in an Affinity System, " Cancer Research 53: 2368–2373 (1993).

Bos et al. "In Vitro Evaluation of DNA–DNA Hybridization as a Two–Step Approach in Radioimmunotherapy of Cancer," Cancer Research 54: 3479–3486 (1994).

Losman et al. "Mimicry of a Carcinoembryonic Antigen Epitope by a Rat Monoclonal Anti–idiotype Antibody," Int. J. Cancer 56: 580–584 (1994).

Sharkey, et al. "Enhanced Clearance of Radiolabeled Murine Monoclonal Antibody by a Syngeneic Anti–Idiotype Antibody in Tumor–Bearing Nude Mice," Int. J. Cancer 51: 266–273 (1992).

Goodwin, D. A. et al., "Pre–Targeted Immunoscintigraphy of Murine Tumors with Indium–111–Labeled Bifunctional Haptens", The Journal of Nuclear Medicine, 29:226–234 (1988).

Hnatowich, D. J. et al., "Investigations of Avidin and Biotin for Imaging Applications", The Journal of Nuclear Medicine, 28:1294–1302 (1987).

Oehr, P. et al., "Streptavidin and Biotin as Potential Tumor Imaging Agents", The Journal of Nuclear Medicine, 29:728–729 (May 1988).

Yuan, Fan, "Pharmacokinetic Analysis of Two–Step Approaches Using Bifunctional and Enzyme–conjugated Antibodies", Cancer Research 51, 3119–3130 (Jun. 15, 1991).

Paganelli, G., "In Vivo Labelling of Biotinylated Monoclonal Antibodies by Radioactive Avidin: A Strategy to Increase Tumor Radiolocalization", Int. J. Cancer: Supplement 2, 121–125 (1988).

Primary Examiner—Sheela Huff
Attorney, Agent, or Firm—Foley & Lardner

[57] ABSTRACT

A radionuclide-chelator conjugate composition for detecting and/or treating lesions in a patient in a pre-targeting protocol which comprises pre-targeting the target cell, tissue, or pathogen with a substrate, using a targeting protein that specifically binds a marker substance on the target cell, tissue, or pathogen and to which the substrate is directly or indirectly bound; parenterally injecting the detection or therapeutic composition of the invention which comprises a chelate conjugate of biotin, a chelator, and a chelatable detection or therapeutic agent, and allowing the composition to accrete at the targeted cell, tissue, or pathogen; wherein the chelate conjugate is purified by chromatography after chelate formation, or further comprises a blood transit-modifying linker or addend that is covalently bound within the chelate conjugate, or both; and using the detection or therapeutic agent to detect or treat the targeted cell, tissue, or pathogen.

42 Claims, No Drawings

DOTA-BIOTIN DERIVATIVES

RELATED APPLICATIONS

This application is a continuation-in-part of U.S. patent application Ser Nos. 08/486,166, filed Jun. 7, 1995, now abandoned, and 08/688,781, filed Jul. 31, 1996, which is a continuation-in-part of co-pending U.S. patent application Ser. No. 08/409,960, filed Mar. 23, 1995, which is a continuation of U.S. patent application Ser. No. 08/062,662, filed May 11, 1993, now abandoned. The entire contents of these patent applications are incorporated herein by reference.

BACKGROUND OF THE INVENTION

1. Field of the Invention

The present invention relates to novel metal-chelator conjugates which comprise a biotin or avidin derivative linked to 1,4,7,10-tetraazacyclododecane-N, N', N", N'"-tetraacetic acid (DOTA). The derivatives are useful, for example, for targeting radiometals to specific sites in vivo using pretargeting protocols for the detection and treatment of tumors, lesions, and sites of infection.

2. Description of Related Art

Metal detection and therapeutic agents can be targeted to in vivo target sites, such as tumors, lesions, and sites of infection, using pretargeting protocols. In pretargeting protocols, a primary targeting species comprising (i) a first targeting moiety which binds to the target site and (ii) a binding site that is available for binding by a subsequently administered second targeting species is targeted to an in vivo target site. Once sufficient accretion of the primary targeting species is achieved, a second targeting species comprising (i) a diagnostic or therapeutic agent and (ii) a second targeting moiety, which recognizes the available binding site of the primary targeting species, is administered. An illustrative example of a pretargeting protocol is the biotin-avidin system for administering a cytotoxic radionuclide to a tumor. In a typical procedure, a monoclonal antibody targeted against a tumor-associated antigen is conjugated to avidin and administered to a patient who has a tumor recognized by the antibody. Then the therapeutic agent, e.g., a chelated radionuclide covalently bound to biotin, is administered. The radionuclide, via its attached biotin is taken up by the antibody-avidin conjugate pretargeted at the tumor. Examples of pre-targeting biotin/avidin protocols are described, for example, in Goodwin et al., U.S. Pat. No. 4,863,713; Goodwin et al., *J. Nucl. Med.* 29:226, 1988; Hnatowich et al., *J. Nucl. Med.* 28:1294, 1987; Oehr et al. 4, *J. Nucl. Med.* 29:728, 1988; Klibanov et al.,*J. Nucl. Med.* 29:1951, 1988; Sinitsyn et al., *J. Nucl. Med.* 30:66, 1989; Kalofonos et al., *J. Nucl. Med.* 31:1791, 1990; Schechter et al., *Int. J. Cancer* 4 48:167, 1991; Paganelli et al., *Cancer Res.* 51:5960, 1991; Paganelli et al., *Nucl. Med. Commun.* 12:211, 1991; Stickney et al., *Cancer Res.* 51:6650, 1991; and Yuan et al., *Cancer Res.* 51:3119, 1991; all of which are incorporated by reference herein in their entirety.

Three-step pretargeting protocols in which a clearing agent is administered after the first targeting composition has localized at the target site also have been described. The clearing agent binds and removes circulating primary conjugate which is not bound at the target site, and prevents circulating primary targeting species (antibody-avidin or conjugate, for example) from interfering with the targeting of active agent species (biotin-active agent conjugate) at the target site by competing for the binding sites on the active agent-conjugate. When antibody-avidin is used as the primary targeting moiety, excess circulating conjugate can be cleared by injecting a biotinylated polymer such as biotinylated human serum albumin. This type of agent forms a high molecular weight species with the circulating avidin-antibody conjugate which is quickly recognized by the hepatobiliary system and deposited primarily in the liver.

Examples of these protocols are disclosed, e.g., in Axworthy et al., PCT Application No. WO 93/25240; Paganelli et al., "Monoclonal Antibody Pretargeting Techniques For Tumour Localization: The Avidin-Biotin System", *Nucl. Med. Comm.*, Vol. 12:211–234, (1991); Oehr et al., "Streptavidin And Biotin As Potential Tumor Imaging Agents", *J. Nucl. Med.*, Vol. 29:728–729, (1988); Kalofonos et al., "Imaging Of Tumor In Patients With Indium-111-Labeled Biotin And Streptavidin-Conjugated Antibodies: Preliminary Communication", *J. Nucl. Med.*, Vol 31:1791–1796, (1990); Goodwin et al., "Pre-Targeted Immunoscintigraphy Of Murine Tumors With Indium-111-Labeled Bifunctional Haptens",*J. Nucl. Med.*, Vol. 29:226–234, (1988). Improved pretargeting protocols using the biotin-avidin system are disclosed, e.g., in our U.S. Pat. Nos. 5,525,338 and 5,482,698 and co-pending U.S. patent applications Ser. Nos. 08/486,166 and 08/731,107, the disclosures of which are incorporated by reference herein in their entirety.

Many of the above-described pretargeting protocols use conjugates comprising biotin and a chelated metal to deliver metal detection and/or therapeutic agents to target sites. One chelating agent, 1,4,7,10-tetraazacyclododecane-N, N, N", N'"-tetraacetic acid (DOTA), is of particular interest because of its ability to chelate a number of diagnostically and therapeutically important metals, such as radionuclides and radiolabels.

Conjugates of DOTA and proteins such as antibodies have been described. For example, U.S. Pat. No. 5,428,156 teaches a method for conjugating DOTA to antibodies and antibody fragments. To make these conjugates, one carboxylic acid group of DOTA is converted to an active ester which can react with an amine or sulfhydryl group on the antibody or antibody fragment. Lewis et al., *Bioconjugate Chem.* 5: 565–76 (1994), describes a similar method wherein one carboxyl group of DOTA is converted to an active ester, and the activated DOTA is mixed with an antibody, linking the antibody to DOTA via the $\epsilon$-amino group of a lysine residue of the antibody, thereby converting one carboxyl group of DOTA to an amide moiety.

Conjugates of DOTA and biotin have been described, but many of these require complicated synthesis steps or are not stable in vivo. For example, Su, *J. Nucl. Med.*, 36 (5 Suppl):154P (1995), discloses the linkage of DOTA to biotin via available amino side chain biotin derivatives such as DOTA-LC-biotin or DOTA-benzyl-4-(6-amino-caproamide)-biotin. However, these biotin derivatives have been shown to be unstable in blood serum.

Yau et al., WO 95/15335, disclose a method of producing nitro-benzyl-DOTA compounds which can be conjugated to biotin. The method comprises a cyclization reaction via transient projection of a hydroxy group; tosylation of an amine; deprotection of the transiently protected hydroxy group; tosylation of the deprotected hydroxy group; and intramolecular tosylate cyclization. This reaction scheme is very lengthy and complicated and the resulting product comprises at least one chiral carbon and may suffer from such problems as, unequal stability and reactivity of enantiomers.

Wu et al., *Nucl. Med. Biol.*, Vol. 19 (2):239–44 (1992), discloses a synthesis of macrocyclic chelating agents for radiolabeling proteins with [111]IN and [90]Y. Wu et al. makes a labeled DOTA-biotin conjugate to study the stability and biodistribution of conjugates with avidin, a model protein for studies. This conjugate was made using a biotin hydrazide which contained a free amino group to react with an in situ generated activated DOTA derivative. Although the DOTA-biotin-avidin conjugates were found to be stable, the resultant $^{90}$Y-labeled and the resultant $^{111}$In labeled compounds achieved only 12% and 29% binding under avidin, respectively, even when incubated with excess avidin.

There is a need, therefore, for a DOTA-biotin conjugate suitable for in vivo use that is stable, readily synthesized, and that can bind avidin efficiently.

SUMMARY OF THE INVENTION

One object of the present invention relates to a metal-chelator conjugate of the formula:

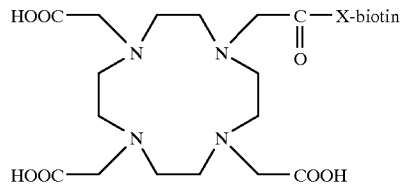

wherein X is a linker wherein said linker is selected from the group consisting of a non-charged polymer, a charged polymer, a polypeptide, and one or more amino acids.

A second object of the present invention relates to a metal-chelate of the formula:

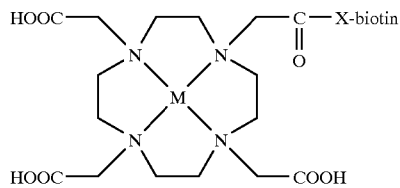

wherein X comprises one or more amino acids; and M is a metal selected from the group consisting of a radionuclide, label, a paramagnetic metal or a heavy metal.

A third object of the present invention relates to a method of treating cancer, infectious diseases, or cardiovascular diseases by administering to a patient an effective amount of a metal chelate of the present invention as part of a pre-targeting protocol.

A fourth object of the present invention relates to a method for enhancing internal or external detection of lesions, cancers, infectious diseases, and cardiovascular diseases by administering an effective amount of a metal chelate of the present invention as part of a pre- targeting protocol.

A fifth object of the invention relates to a process for preparing the conjugates of the formula:

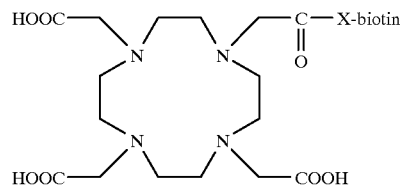

wherein X comprises one or more amino acids comprising:
(a) reacting 1,4,7,10-tetraazacyclododecane N, N', N", N'''-tetraacetic acid with N-hydroxysulfosuccinimide in a solution of 1-ethyl-3-[3-dimethylamino) propyl] carbodiimide to yield the N-hydroxysuccinimide ester of DOTA;
(b) reacting the product obtained in (a) with biotin-X-NH$_2$, wherein X is as defined above; and
(c) isolating the biotin-amino acid-DOTA product; and optionally, further reacting the coupled product obtained in step (c) with a solution of a metal cation; and isolating the product from unchelated metal.

DETAILED DESCRIPTION OF THE INVENTION

The present invention provides a metal-chelator conjugate comprising a biotin and 1,4,7,10-tetraazacyclododecane-N, N, N", N'''-tetraacetic acid (DOTA), and having the following formula:

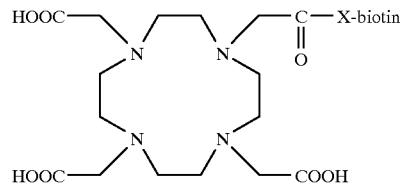

wherein X comprises a linker moiety, and preferably comprises one or more amino acids.

The invention also provides a chelated complex comprising the DOTA-biotin conjugate chelated to a metal wherein the metal is a radionuclide, label, paramagnetic metal or a heavy metal.

An insight leading to the present invention stemmed from a kinetic analysis of the therapeutic agent delivery in the pre-targeting system. A central problem in this field has been the difficulty of accreting high amounts of therapeutic agent at a target site. Antibody targeting has improved the specificity of targeting, but has not completely overcome the specific activity problem.

As an example, $3.25 \times 10^{14}$ molecules of antibody-avidin conjugate were found to bind per gram of tumor in a nude mouse/human xenograft animal model of colorectal cancer. About one in ten of the theoretical biotin binding sites placed at the tumor via the antibody-avidin conjugate were subsequently targeted with biotin moieties. In addition, due to low specific activity of the biotin-chelate, only about one in 350 of those biotin residues was actually associated with a radionuclide atom.

The radionuclide-chelator-biotin conjugate of the present invention helps to solve this low specific activity problem. Due to a nuclide's cationic nature, the small size of biotin, and the small size of most chelators, a chelated biotin conjugate that contains the nuclide can be conveniently purified away from a conjugate that lacks the nuclide.

Consequently, a therapeutic agent composition of much higher specific activity can be delivered to a target site.

The present inventors also have found that controlling the size and clear rate of the metal chelate also can optimize specific activity. The excretion of a substance that is filtered, but not reabsorbed or secreted by the kidney is controlled by the sieving properties of the kidney glomerular wall. How well the kidney excretes such a substance can be determined by measurements of the clearance of a test molecule, relative to some "freely permeable" reference polymer such as inulin, as summarized by Brenner et al. in *Am. J. Physiol.* 234: F455–60 (1978), which is herein incorporated in its entirety by reference. The ratio of urinary clearance of a test solute to a reference solute is equal to the ratio of the concentration of the test solute in Bowman's space to its concentration in plasma water. This ratio is called the "fractional clearance" of the test solute. The fractional clearance varies from 0, when test molecules cannot enter the kidney filtrate, to 1 when they encounter no measurable restriction to filtration.

A metal chelate that has a fractional clearance near 1 is quickly cleared by the kidney (if not readsorbed by the kidney) and has a short body residence time, i.e. fast renal clearance. A metal chelate that has a fractional clearance near zero typically is cleared slowly by the liver or other tissue, and has a longer body residence time, i.e. slow renal clearance. In practice, it is preferred to modify the metal chelate by selection of a linker that gives the metal chelate a fractional clearance of an intermediate value between 1 and 0. More preferred is a fractional clearance between 0.2 and 0.8.

A skilled artisan can estimate what size of polymer and what kinds of charges are most suitable for the linker, based on the predicted size, i.e. the effective molecular radius, of the completed metal chelate. Alternately, fractional clearances can be determined by experimentation.

The term "effective molecular radius" refers to what size a molecule displays in solution. This value easily is determined by a skilled artisan. A preferred method to determine the effective molecular radius of a molecule is quantitative gel chromatography as taught by Chang et al. in *Kidney Intern.* 8: 212–18 (1975) and in *Biophys. J.* 15: 887–906 (1975).

Uncharged polymers such as dextran have a fractional clearance of 1 when they have an effective molecular radius of about 18 angstroms or less. Such polymers have a fractional clearance of about 0 when they have an effective molecular radius of about 44 angstroms or more.

For purposes of the present invention, a non-charged polymer such as polyethylene glycol or dextran which is not reabsorbed by the kidney can be a linker. In this case the biotin-linker-chelator-nuclide conjugate should have an effective molecular radius of more than 18 angstroms in order to prolong its body residence time, compared to a small molecule that is filtered without restriction by the kidney. The metal chelate should, at the same time, have an effective molecular radius of less than about 44 angstroms in order that the kidney gradually clear it from blood. If the effective molecular radius is significantly more than 44 angstroms then the body residence time will be too long and a mechanism different from kidney clearance may dispose of the metal chelate.

The selected linker can have one or more negative charges. If a polyanionic linker, such as, for example, dextran sulfate is used, then the metal chelate size should be smaller to obtain the same degree of fractional clearance by the kidney. For example, a dextran polymer-based metal chelate having an effective molecular radius of 18 angstroms will have a fractional clearance of about 1 (quickly removed by passing through the kidney), but a dextran sulfate-based metal chelate having an effective molecular radius of 18 angstroms will have a fractional clearance closer to 0.5, and will be removed from the blood more slowly.

The selected linker can have one or more positive charges. A positively charged linker such as a short polypeptide having lysine and/or arginine residues will effect more rapid kidney clearance of the chelate conjugate.

In practice, the size and charge of the complete conjugate made from biotin, linker, chelator, and chelated detection or therapeutic agent is considered when estimating fractional clearance. However, when biotin is used with the preferred chelator DOTA, or another small chelator, the linker may dominate the chelate conjugate's blood residence time.

For a neutrally charged chelator conjugate, the linker should be chosen such that the chelator conjugate's effective molecular radius is between about 18 and about 42 angstroms. For anionic chelator conjugates, the effective molecular radius should be smaller, depending on how many excess negative charges are in the chelate conjugate. For very anionic chelator conjugates, the effective molecular radius should be between about 15 and about 32 angstroms. When the chelator conjugate is to have a net positive charge, the linker should be chosen to give a slightly greater effective molecular radius of the chelator conjugate in comparison to that for neutrally charged chelate conjugates.

Blood residence time also can be controlled by altering the linker's hydrophobicity. Polypeptides are preferred for this use. One or more hydrophobic amino acid residues such as phenylalanine, tryptophan, tyrosine, leucine, isoleucine, or valine in the peptide linker will increase the hydrophobicity of the chelate conjugate. Adding one or more hydrophobic residues to the chelator conjugate can both alter the effective molecular radius of the chelator conjugate and increase the chances that the chelator conjugate will interact with other proteins in the blood.

While not wishing to be bound by a particular theory of the invention, it is believed that one mechanism for prolonging the blood residence time of small chelator conjugates that contain hydrophobic residue(s) is the ability of the chelator conjugate to associate with serum albumin and escape filtration by the kidney. In this context, a chelator conjugate having one or more hydrophobic residues, such as for example, a long aliphatic chain, a phenyl ring, an imidazole, and the like, may have affinity for the hydrophobic binding site of serum albumin. Alternative chelator conjugates can be tested for their relative blood residence times by comparing how well they associate with serum albumin. A carrier that has hydrophobic residue(s) is particularly suited for the formation of a detection or therapeutic chelator conjugate that provides a detection or delivery agent over a longer time period.

Many short peptides can be made and are contemplated for use as linkers in this invention. In fact, virtually all combinations of amino acids that are shorter than 400 amino acid residues long could be employed for some purposes as a linker. Preferred are short polypeptides of less than about 50 amino acid residues, and most preferably less than ten residues. Especially preferred are peptides that contain a basic amino acid such as lysine, which, for some nuclides, can balance out a negatively charged chelate.

A second insight leading to the present invention involved the modification of previously described biotin-chelator conjugates to alter their stability. Stability studies of various biotinylated chelators indicate that many are subject to the action of native biotinidase. The present inventors have determined that it is advantageous to link biotin to a chelator, such as DOTA, using a non-natural amino acid or other linker that is resistant to biotinidase.

Unfortunately, a biotin-amide linkage has been found to be unstable, even in vitro in the presence of human serum. D-amino acids and D-amino acid peptides can form more stable linkages between biotin and chelators and are preferred alternatives.

The advantages of incorporating one or more D-amino acid containing bonds between chelator and biotin can be summarized as follows:

1) The peptide bond between biotin and a D-amino acid is stable towards biotinidase. This prevents undesired separation of biotin from the detection or therapeutic agent in human serum.
2) One or more D-amino acids can be used to link biotin and a chelator. The peptide's hydrophobicity can be adjusted for example, by increasing the number of phenylalanines or other hydrophobic residues within the linker to achieve a desired body residence time.
3) The number of chelators per biotin can be increased by coupling more chelators, through multiple amino acid residues, in the linker. The primary amino acid residues of lysine are a preferred embodiment in this context. By attaching one chelator per lysine residue, and incorporating multiple lysine residues in the biotin-peptide the specific activity of the chelate conjugate can be increased.
4) A biotinylated peptide can be synthesized easily by a manual solid phase technique or by an automated peptide synthesizer.

D-amino acids are preferred for chelator conjugates with good serum stability. Peptide bonds formed from the D-amino acids are much less susceptible to proteolysis, and chelator conjugates made from D-amino acids persist longer in the circulation.

Examples of biotin-polypeptide-chelator conjugates include:

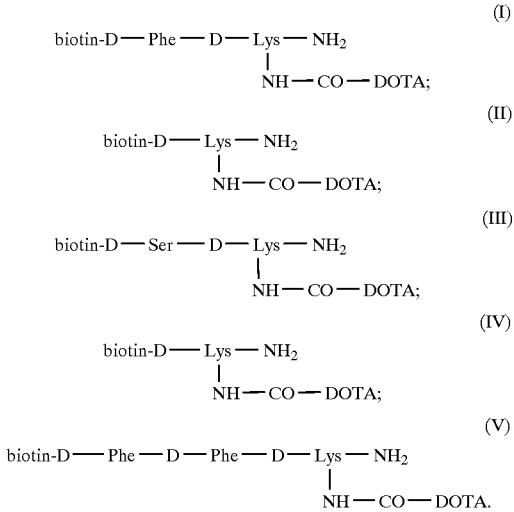

The optimum body residence time for a given set of conditions can be determined experimentally. A factor in the optimum body residence time however, when using a nuclide detection or therapeutic agent, is the half-life of the isotope used. A very short half-life nuclide works best in combination with chelator conjugates that are cleared more rapidly by the kidney. A chelator conjugate that exhibits a small effective molecular radius and which is not very hydrophobic will exhibit a short body residence time.

Linkers that cause a fractional clearance of near 0 or that cause the chelator conjugate to bind to serum protein are more preferred for long half-life isotopes. This kinds of reagent would behave like a time-release capsule and slowly localize at the target site.

The use of a hydrophobic linker can prolong the serum half life of the detection or therapeutic metal chelate agent. Consequently, an isotope of shorter tissue range (lower decay energy) and longer half-life can be employed to spare blood and marrow cells while delivering a sustained dose-level to a target. The methodology used in this approach, in essence, allows the choice of possible radiotherapeutic isotopes to be expanded considerably.

In a preferred embodiment, a DOTA-peptide-biotin chelator conjugate having a net charge of 3− at physiological pH is used to chelate a metal (+3) cation and form a neutral chelate conjugate. The metal-containing chelate is purified from non-metal-containing chelator by anion exchange chromatography.

Avidin and biotin species useful in the present invention are known in the art.

"Biotin", can be, inter alia, modified by the addition of one or more addends, usually through its free carboxyl residue. Useful biotin derivatives include active esters, amines, hydrazides and thiol groups that are coupled with a complimentary reactive group such as an amine, an acyl or alkyl group, a carbonyl group, an alkyl halide or a Michael-type acceptor on the appended compound or polymer.

Among the radionuclides and labels useful in the radionuclide-chelator-biotin conjugates of the present invention, gamma-emitters, positron-emitters, x-ray emitters and fluorescence-emitters are suitable for localization and/or therapy, while beta and alpha-emitters and electron and neutron-capturing agents, such as boron and uranium, also can be used for therapy. In addition to nuclides, cytotoxic drugs that can become chelated are known to those skilled in the art and are useful for the present invention. Suitable compounds can be found in compendia of drugs and toxins, such as the Merck Index, Goodman and Gilman, and the like, and in the references cited above.

Useful diagnostic radionuclides include Ruthenium-95, Ruthenium-97, Ruthenium-103, Ruthenium-105, Technetium-99m, Mercury-197, Gallium-67, Gallium-68, Osmium-191, Indium-111, Indium-113 and Lead-203. Useful therapeutic radionuclides include Antimony-119, Actinium-225, Rhenium-186, Rhenium-188, Rhenium-189, Silver-111, Platinum-197, Palladium-103, Palladium-109, Copper-67, Yttrium-90, Scandium-47, Samarium-153, Lutetium-177, Rhodium-105, Praseodymium-142, Praseodymium-143, Terbium-161, Holmium-166, Lead-212, Bismuth-212, Gold-198 and Gold-199.

In a pretargeting protocol, a primary targeting species (which is not bound to a diagnostic or therapeutic agent) comprising a first targeting moiety which binds to the target site and a binding site that is available for binding by a subsequently administered second targeting species is targeted to an in vivo target site. Once sufficient accretion of the primary targeting species is achieved, a second targeting species comprising a diagnostic or therapeutic agent and a second targeting moiety, which recognizes the available binding site of the primary targeting species, is administered. Such pre-targeting procedures utilize targeting protein to locate a biotin detection or therapeutic agent to a target site. The targeting protein comprises a protein, peptide, polypeptide, glycoprotein, lipoprotein, or the like, e.g. hormone, lymphokine, growth factor, albumin, cytokine, enzyme, immune modulator, receptor protein, antibody and antibody fragment.

An illustrative example of a pretargeting protocol is the use of the biotin-avidin system to administer a cytotoxic radioantibody to a tumor. In a typical procedure, a monoclonal antibody targeted against a tumor-associated antigen is conjugated to avidin (or biotin) and administered to a patient who has a tumor recognized by the antibody. Then the therapeutic agent, e.g., a chelated radionuclide covalently bound to biotin is administered. The radionuclide, via its attached biotin, is taken up by the antibody-avidin conjugate pretargeted to the tumor. During use, the detection or therapeutic biotin-chelate is injected parenterally after a pretargeted antibody-avidin conjugate has had time to localize to a targeted cell, tissue or pathogen. Alternatively, the biotin-chelate detection or therapeutic agent is injected after the clearing and localizing agent in a 3-step protocol. Parenteral administration comprises intravenous, intraarterial intrapleural, intraperitoneal, intrathecal, subcutaneous and perfusion administration.

The detection or therapeutic metal chelate agent binds prelocalized antibody-conjugate by virtue of the avidin-biotin binding reaction between an avidin and the biotin of the detection or therapeutic metal chelate agent.

A physiological solution of the biotin-chelator conjugate is advantageously metered into sterile vials, e.g., at a unit dosage of about 0.1–500 mg of the chelator conjugate, and the vials are either stoppered, sealed and stored at low temperature, or lyophilized, stoppered, sealed and stored. The vial contents can be reconstituted with a solution containing the metal ion to be chelated.

During use within a pre-targeting protocol, the detection or therapeutic agent-chelator conjugate preferably is purified immediately prior to use. When a relatively stable detection or therapeutic agent is used, however, purification to increase its specific activity can be performed prior to storage.

Avidin, found in egg whites, has a very high binding affinity for biotin, which is a B-complex vitamin (Wilcheck et al., *Anal. Biochem,* 171:1, 1988). Streptavidin, derived from *Streptomyces avidinii*, is similar to avidin, but has lower non-specific tissue binding, and therefore often is used in place of avidin. As used herein "avidin" includes all of its biological forms either in their natural states or in their modified forms. Modified forms of avidin which have been treated to remove the protein's carbohydrate residues ("deglycosylated avidin"), and/or its highly basic charge ("neutral avidin"), for example, also are useful in the invention. Both avidin and streptavidin have a tetravalency for biotin, thus permitting amplification when the former bind to biotin. Four detection or therapeutic agents, such as nuclides, can be attached to each targeting protein.

The improved metal-chelated conjugates of the present invention can be used in the detection (either by internal procedures or by external imaging) and/or treatment of lesions, including cancers, infectious diseases, cardiovascular diseases and other pathological conditions as part of a pre-targeting procedure.

Internal detection procedures in the context of the invention comprise intraoperative, intravascular or endoscopic, including laparoscopic, techniques, both surgically invasive and non-invasive. Examples of appropriate applications are provided in the above-referenced and incorporated Goldenberg patents and applications.

Examples of cancer states which can be detected and treated in accordance with the invention include carcinomas, melanomas, sarcomas, neuroblastomas, leukemias, lymphomas, gliomas and myelomas.

Examples of infectious diseases which can be detected and treated in accordance with the invention include those caused by invading microbes or parasites. As used herein, "microbe" denotes virus, bacteria, rickettsia, mycoplasma, protozoa, fungi and like microorganisms, "parasite" denotes infectious, generally microscopic or very small multicellular invertebrates, or ova or juvenile forms thereof, which are susceptible to antibody-induced clearance or lytic or phagocytic destruction, e.g., malarial parasites, spirochetes and the like, including helminths, while "infectious agent" or "pathogen" denotes both microbes and parasites.

The DOTA-biotin conjugates of the present invention can be prepared by the following procedure. A carboxyl group of DOTA is activated by conversion into an ester. The ester is synthesized, for example, by reacting DOTA with, e.g., N-hydroxysulfosuccinimide ester and EDC (1-ethyl-3- [3-dimethylamino)propyl] carbodiimmide. See, for example, Mease et al., U.S. Pat. No. 5,428,156 and Lewis et al., *Bioconjugate Chem.* 5: 565–76 (1994). The resultant ester is then reacted with a free amine containing biotinylating agent which can be represented by biotin-X-NH$_2$, wherein X comprises a linker moiety, preferably one or more amino acids. These biotinylating agents are biotin-linker conjugates and become conjugated to DOTA. The DOTA biotin conjugate is then isolated by preparative chromatography. The biotin-X-NH$_2$ is prepared by reacting a peptide with a free amino group in a solution of an ester of D-biotin. In order to chelate a metal to the biotin-X-DOTA, a solution of a metal cation is coupled with biotin-X-DOTA and the product is then isolated from unchelated metal cations.

Biotinylating agents which are represented by the general formula II in Table 1 can be used in accordance with the above recited process, wherein $R_1$ is hydrogen, substituted alkyl, or substituted aryl group; $R_2$ is a group terminating in a primary or secondary amino group; $R_3$ is carboxyl, a substituted alkyl or substituted aryl group. Substituents on $R_1$ and $R_3$ can be, for example, carboxyl, tertiary amine such as dimethylamino or hydroxyl. These substrates can be prepared by reacting N-hydroxysuccinimidobiotin (see formula III in Table 1, wherein R=succinimidyl) with the appropriate amine of the general formula I in Table 1, wherein $R_1$, $R_2$ and $R_3$ have the same meaning as described above with reference to formula II.

The amine terminus of the biotinylated agents is suitably protected with a protecting group R', with R' being tertiary-butoxycarbonyl, for example, which is deprotected prior to the reaction with a metal-chelating agent or a boron-containing entity.

Some examples of the diamines which can be used for preparing biotinylating agents are shown as formulas Ia, Ib and Ic in Table 1.

TABLE 1

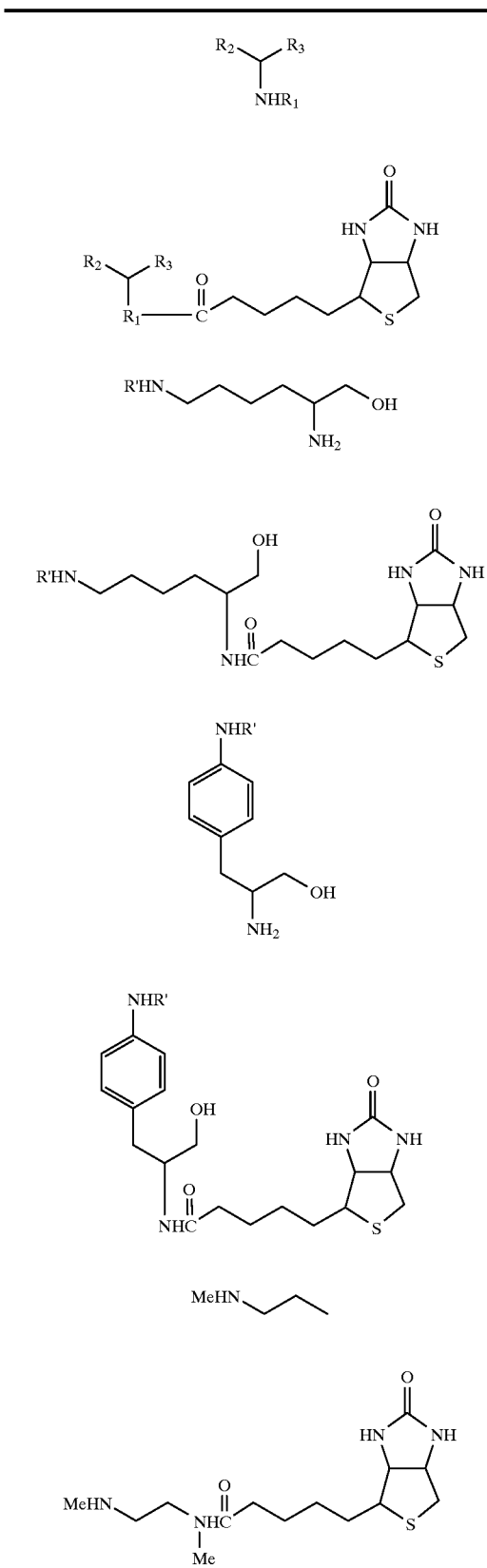

TABLE 1-continued

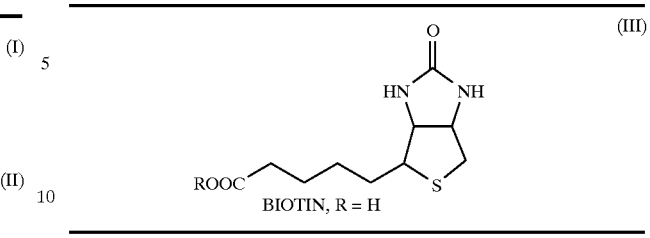

Without further elaboration, it is believed that one skilled in the art can, from the preceding description, utilize the present invention to its fullest extent. The following specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

Example 1- Coupling polypeptide and carbohydrate linkers to Biotin

A- To polypeptide via Lysine.

A polypeptide having at least one free amino group at a concentration of 10 mg/ml in a borate buffer, 0.1M, pH 8.5 is mixed with a 10 fold molar excess of an activated sulfosuccinimide ester of D-biotin. The reaction solution is stirred for 16 hours and kept at a temperature of 25° C. At the end of the reaction period, the modified polypeptide is separated from unbound biotin and other low molecular weight contaminants by size-exclusion or ion exchange chromatography.

B- To Polypeptide via Cysteine.

A polypeptide at a concentration of 10 mg/ml, containing at least one free cysteine residue in phosphate buffer, pH 7.5, is mixed with a 10 fold molar excess of biotin-maleimide (N-biotinyl-N-[6-maleimido hexanoyl]hydrazide) (Sigma Chem. Co.). A DMSO co-solvent is added up to a 20% concentration to facilitate reactant solubility. The reaction solution is stirred for 1 hour at a temperature of about 25° C. At the end of the reaction period, the biotinylated polypeptide is separated from unbound biotin and other low molecular weight contaminants chromatographically.

C- To oxidized dextran

Dextran at a concentration of 1 mg/ml is treated with sodium metaperiodate to a final concentration of 0.03 mg/ml in phosphate buffered saline at room temperature for 4 hours. The oxidized dextran is purified from sodium metaperiodate by size-exclusion chromatography in phosphate buffer, 0.1 M, pH 7.5. The oxidized dextran (1 mg/ml) is reacted with biotin-hydrazide (Pierce Chemical Co.) in 0.1 M phosphate buffer, pH 7.5 for 6 hours at 37° C. After coupling, the formed hydrazone is reduced by the addition of sodium cyanoborohydride with stirring overnight. The biotinylated dextran is purified by size-exclusion chromatography on a G-25 Sephadex column.

Example 2- Preparation of Biotin-D-Phe-D-Lys-DOTA

N-hydroxysuccinimide ester of DOTA (1,4,7,10-tetraazacyclododecane N, N', N", N'"-tetraacetic acid) is prepared by modification of a procedure described by Lewis et al., *Bioconjugate Chem.* 5: 565–76 (1994). Freshly prepared EDC (3-ethyl-3-[3-(dimethyl-amino) propyl] carbodiimide) in $H_2O$ (12.25 mg in 40 µl, 64 µmol) is added to a solution of 60 mg (128 µmol) of trisodium DOTA (Parish Chemicals) and 27.7 mg (128 µmol) of sulfo-NHS (N-hydroxysuccinimide) in 960 µL of $H_2O$ at 4° C. The reaction mixture is stirred at 4° C. for 30 minutes. The theoretical concentration of active ester in the reaction mixture is 64 mM.

The peptide biotin-D-Phe-D-Lys-$NH_2$ (16.6 mg, 32 µmol) is added to the above solution and the pH is adjusted to 8.5 with 6 M NaOH. The solution is stirred for 18 hours at 4° C. The product is isolated by purification on a preparative reverse-phase C18 column.

Example 3 - Chelating Gadolinium into biotin-peptide-DOTA for MRI

A solution of biotinyl-peptide-DOTA is treated with a 0.01–1 mol solution of gadolinium cation in acetate buffer at a pH of 5 for 3 hours at 37° C. The metallated biotin-peptide-DOTA is separated from unincorporated metal chromatographically.

Example 4
Coupling a Biotinylating Agent of General Formula II with the Metal-Chelating Agent DOTA region-) cdr-grafted version of the IMMU-14 mab], labeled with 5 mCi of I-131 radionuclide (prepared by the iodogen method), in order to determine the localization qualities of the SA-hIMMU-14 conjugate. With strong positive localization indicated from this initial injection, a 0.5 g dose of the SA-IMMU-14 is then infused over a 1 hour period using a sterile, non-pyrogenic, isotonic solution of the conjugate. After 48 hours post-injection of the targeting antibody conjugate, a 0.5 g first antibody-clearing dose of the anti-idiotypic mab, hWI2, is infused in a similar manner. Four hours after administration of the hWI2, an infusion of 200 mCi of the therapy agent, Y-90-(2-biotinylmethylamidoethyl) methylamido-DOTA, dissolved in 200 ml of phosphate buffered saline containing 1% v/v human serum albumin is begun. The patient is monitored for adverse reactions during the infusion of the isotope. After the infusion is complete the patient's blood and urine are analyzed and quantified for the presence of radioyttrium out to 48 hours post-injection, to determine the amount of isotope in circulation and the amount eliminated via the urine. The patient is observed periodically for the next two years, during which time the cancer exhibits a full response to the treatment over this extended period of time. (2-biotinylmethylamidoethyl)methylamido-DOTA:

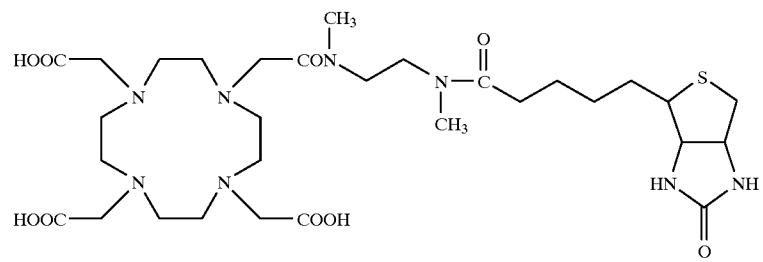

1,4,7,10-Tetraazacyclododecane N, N', N", N'''-tetraacetic acid (DOTA) forms kinetically stable chelates with metal ions of lanthanide series (such as yttrium and gadolinium) of the periodic table. DOTA N-hydroxysulfosuccinimide ester is prepared following a known procedure (Lewis M. R., et al., *Bioconjugate Chem.*, 5: 565–576, 1994), by mixing 60 mg (128 µmol) of trisodium DOTA and 27.7 mg. (28 µmol) of N-hydroxysulfosuccinimide, in 0.96 ml of water, and incubating this solution with 49 µl of a freshly prepared solution of 'EDC' (50 mg/ml) at 4° C. for 30 min. 1 ml of this solution contains 12.68 µmol (theoretical) of the mono-activated DOTA sulfosuccinimide.

An excess of this reagent is reacted with any of the amine-deprotected biotinylating reagent shown in Table 1, and stirred at 4° C. for a period of 18–24 hours. The biotinylated DOTA product is purified on a reverse phase preparative HPLC column using acetonitrile-water gradient-elution at a flow rate of 1ml/min and monitoring the eluent with a refractive index detector. The purified material is analyzed by NMR spectroscopy and mass spectrometry.

Example 5

Treatment of Human Cancer Using an Alternate Procedure.

A patient presenting a carcinoembryonic antigen (CEA)-producing cancer is treated with a 1 mg dose of I-131-SA-hIMMU-14 [SA-hIMMU14 is a conjugate corresponding to streptavidin-humanized (complementarity determining It will be apparent to those skilled in the art that various modifications and variations can be made to the processes and compositions of this invention. Thus, it is intended that the present invention cover the modifications and variations of this invention provided they come within the scope of the appended claims and their equivalents.

What is claimed is:

1. A metal-chelator conjugate of the formula:

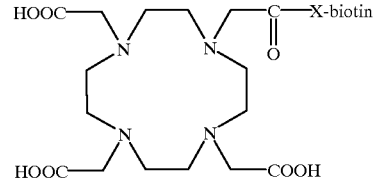

wherein X comprises a linker wherein said linker is selected from the group consisting of a non-charged polymer, a charged polymer, a polypeptide, and one or more amino acids.

2. The metal-chelator conjugate of claim 1, wherein X comprises a non-charged polymer.

3. The metal chelator conjugate of claim 1, wherein X comprises a charged polymer.

4. The metal-chelator conjugate of claim 1, wherein X comprises a polypeptide.

5. The metal-chelator conjugate of claim 1, wherein X comprises one or more amino acids.

6. The metal chelator conjugate of claim 3, wherein said charged polymer is a positively charged polymer.

7. The metal-chelator conjugate of claim 3, wherein said charged polymer is a negatively charged polymer.

8. The metal-chelator conjugate of claim 5, wherein said one or more amino acids are one or more D-amino acids.

9. The metal-chelator conjugate of claim 8, wherein said D-amino acids are selected from the group consisting of D-lysine, D-phenylalanine, D-tryptophan, D-tyrosine, D-leucine, D-isoleucine and D-valine.

10. The metal-chelator conjugate of claim 4, wherein said polypeptide contains less than 400 amino acids residues.

11. The metal-chelator conjugate of claim 10, wherein said poypeptide contains less than 50 amino acid residues.

12. The metal-chelator conjugate of claim 10, wherein said polypeptide contains less than 10 amino acid residues.

13. The metal-chelator conjugate of claim 4, wherein said polypeptide is selected from the group consisting of D-Phenylalanine-D-Lysine, D-Serine-D-Lysine, and D-Phenylalanine-D-Phenylalanine-D-Lysine.

14. The metal-chelator conjugate of claim 4, wherein said polypeptide comprises a basic amino acid.

15. The metal-chelator conjugate of claim 1, which is selected from the group consisting of:

[structure: HOOC-cyclen-CH2-C(=O)-NH-D-Lys(NH2)-D-Phe-biotin; with HOOC, HOOC, COOH substituents]

[structure: HOOC-cyclen-CH2-C(=O)-NH-D-Lys(NH2)-biotin]

[structure: HOOC-cyclen-CH2-C(=O)-NH-D-Lys(NH2)-D-Ser-biotin]

and

[structure: HOOC-cyclen-CH2-C(=O)-NH-D-Lys(NH2)-D-Phe-D-Phe-biotin.]

16. The metal-chelator conjugate of claim 1 which is

[structure: HOOC-cyclen-CH2-CON(CH3)-CH2CH2-N(CH3)-C(=O)-(CH2)4-biotin]

17. A metal chelate of the formula:

[structure: cyclen with M in center, HOOC, HOOC, COOH substituents, and CH2-C(=O)-X-biotin]

wherein X comprises a linker selected from the group consisting of a non-charged polymer, a charged polymer, a polypeptide, and one or more amino acids; and M comprises a metal selected from the group consisting of a radionuclide, a label a paramagnetic metal and a heavy metal.

18. The metal chelate of claim 17, wherein said radionuclide is a diagnostic radionuclide.

19. The metal chelate of claim 17, wherein said radionuclide is a therapeutic radionuclide.

20. The metal chelate of claim 18, wherein said diagnostic radionuclide is selected from the group consisting of Ruthenium-95, Ruthenium-97, Ruthenium-103, Ruthenium-105, Technetium-99, Mercury-197, Gallium-67, Gallium-68, Osmium-191, Indium-111, Indium-113 and Lead-203.

21. The metal chelate of claim 19, wherein said therapeutic radionuclide is selected from the group consisting of Antimony-119, Actinium-225, Rhenium-186, Rhenium-188, Rhenium-189, Silver-111, Platinum-197, Palladium-103, Palladium-109, Copper-67, Yttrium-90, Scandium-47, Samarium-153, Lutetium-177, Rhodium-105, Praseodymium-142, Praseodymium-143, Terbium-161, Holmium-166, Lead-212, Bismuth-212, Gold-198 and Gold-199.

22. The metal-chelator conjugate of claim 17, wherein X comprises a non-charged polymer.

23. The metal chelate conjugate of claim 17, wherein X comprises a charged polymer.

24. The metal-chelator conjugate of claim 17, wherein X comprises a polypeptide.

25. The metal-chelator conjugate of claim 17, wherein X comprises one or more amino acids.

26. The metal chelator conjugate of claim 23, wherein said charged polymer is a positively charged polymer.

27. The metal-chelator conjugate of claim 23, wherein said charged polymer is a negatively charged polymer.

28. The metal-chelator conjugate of claim 25, wherein said one or more amino acids are one or more D-amino acids.

29. The metal-chelator conjugate of claim 28, wherein said D-amino acids are selected from the group consisting of D-lysine, D-phenylalanine, D-tryptophan, D-tyrosine, D-leucine, D-isoleucine, and D-valine.

30. The metal-chelator conjugate of claim 24, wherein said polypeptide contains less than 400 amino acids residues.

31. The metal-chelator conjugate of claim 30, wherein said polypeptide contains less than 50 amino acid residues.

32. The metal-chelator conjugate of claim 30, wherein said polypeptide contains less than 10 amino acid residues.

33. The metal-chelator conjugate of claim 24, wherein said polypeptide is selected from the group consisting of D-Phenylalanine-D-Lysine, D-Serine-D-Lysine, and D-Phenylalanine-D-Phenylalanine-D-Lysine.

34. The metal-chelator conjugate of claim 24, wherein said polypeptide comprises a basic amino acid.

35. In a method of treating cancer, infectious diseases, or cardiovascular diseases, wherein in said method, a primary targeting species is administered to said mammal which binds via a primary, target-specific binding site to the target site or to a substance produced by or associated with the target site and which comprises a second binding site which binds an active agent conjugate or to an intermediate which in turn binds an active agent conjugate, sufficient time being allowed for said primary targeting species to localize at the target site;

a clearing agent is then administered that binds to said primary targeting species, sufficient time being allowed for said clearing agent to clear said primary targeting species from circulation; and a metal chelate, comprising a moiety that binds to said second binding site of said primary targeting species and a therapeutic or detection metal, is then administered to said mammal in an effective amount, sufficient time being allowed for said metal chelate to localize at said target site, the improvement wherein said metal chelate is according to claim 17.

36. In a method of enhancing internal or external detection of lesions, cancers, infectious diseases, and cardiovascular diseases, wherein in said method, a primary targeting species is administered to said mammal which binds via a primary, target-specific binding site to the target site or to a substance produced by or associated with the target site and which comprises a second binding site which binds an active agent conjugate or to an intermediate which in turn binds an active agent conjugate, sufficient time being allowed for said primary targeting species to localize at the target site;

a clearing agent is then administered that binds to said primary targeting species, sufficient time being allowed for said clearing agent to clear said primary targeting species from circulation; and a metal chelate, comprising a moiety that binds to said second binding site of said primary targeting species and a therapeutic or detection metal, is then administered to said mammal in an effective amount, sufficient time being allowed for said metal chelate to localize at said target site, the improvement wherein said metal chelate is according to claim 17.

37. In the method of claim 35 wherein the cancer being treated is selected from the group consisting of carcinoma, melanoma, sarcoma, neuroblastoma, leukemia, lymphoma, glioma and myeloma.

38. In the method of claim 35 wherein the infectious disease being treated is selected from the group consisting of microbial disorders and parasitic disorders.

39. In the method of claim 36 wherein the internal detection is selected from the group consisting of intraoperative, intravascular, and endoscopic detection.

40. A process for preparing the conjugates of the formula:

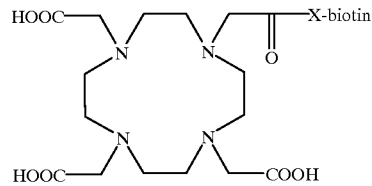

wherein X comprises a linker selected from the group consisting of a non-charged polymer, a charged polymer, a polypeptide, and one or more amino acids, comprising:

(a) reacting 1,4,7,10-tetraazacyclododecane N, N', N", N'''-tetraacetic acid with N-hydroxysulfosuccinimide in a solution of 1-ethyl-3-[3-(dimethylamino)propyl] carbodiimide to yield the N-hydroxysuccinimide ester of 1,4,7,10-tetraazacyclododecane N, N', N", N'''-tetraacetic acid;

(b) reacting the product obtained in (a) with biotin-X-NH$_2$, wherein X is as defined above; and (c) isolating the resultant product.

41. A process according to claim 40 further reacting the coupled product obtained in step (c) with a solution of a metal cation; and isolating the product from unchelated metal.

42. A process according to claim 40 wherein said biotin-X-NH$_2$ is prepared by reacting a peptide with a free amino group in a solution of a sulfosuccinimide ester of D-biotin.

* * * * *